United States Patent [19]
Bossert et al.

[11] 3,966,948
[45] June 29, 1976

[54] SPASMOLYTIC, VASO-DILATING AND ANTI-HYPERTENSIVE COMPOSITIONS AND METHODS

[75] Inventors: Friedrich Bossert, Wuppertal-Elberfeld; Wulf Vater, Opladen, both of Germany

[73] Assignee: Bayer Aktiengesellschaft, Germany

[22] Filed: July 3, 1974

[21] Appl. No.: 485,333

Related U.S. Application Data

[62] Division of Ser. No. 344,277, March 23, 1973, abandoned, which is a division of Ser. No. 107,849, Jan. 19, 1971, Pat. No. 3,775,422.

[30] Foreign Application Priority Data
Jan. 24, 1970 Germany.......................... 2003146

[52] U.S. Cl............................... 424/266; 424/251; 424/263
[51] Int. Cl.² ....................................... A61K 31/455
[58] Field of Search ............ 424/263, 266, 251, 260

[56] References Cited
UNITED STATES PATENTS
3,647,807  3/1972  Bossert et al. ............... 260/295.5 R OTHER PUBLICATIONS
Merck Index, 7th Ed. p. 1434, (1960).

*Primary Examiner*—Norman A. Drezin

[57] ABSTRACT

1,4-Dihydropyridines of the formula:

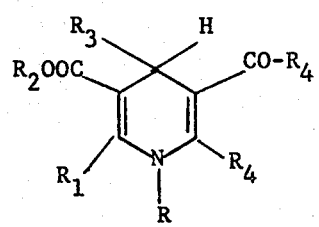

wherein

R is hydrogen, straight, branched or cyclic lower alkyl, lower alkenyl, or lower alkinyl, unsubstituted or substituted by hydroxyl or alkoxy of 1 to 3 carbon atoms; or benzyl, or phenethyl, unsubstituted or substituted in the aryl portion by 1 to 7 members selected from the group consisting of 1 to 3 alkoxy moieties of 1 to 3 carbon atoms, 1 or 2 alkyl moieties of 1 to 3 carbon atoms, and 1 or 2 halogen atoms;

$R_1$ is straight or branched chain alkyl of 1 to 4 carbon atoms;

$R_2$ is straight or branched chain alkyl of 1 to 6 carbon atoms, straight or branched chain dialkyl of 1 to 6 carbon atoms, straight or branched chain alkenyl of 2 to 6 carbon atoms, straight or branched chain alkinyl of 2 to 6 carbon atoms, cyclic alkyl of 3 to 6 carbon atoms, cyclic alkenyl of 3 to 6 carbon atoms, straight or branched chain alkyl or alkenyl of 2 to 6 carbon atoms interrupted by 1 or 2 oxygen atoms, straight or branched chain alkyl of 1 to 6 carbon atoms substituted by hydroxyl, or straight or branched chain alkenyl of 2 to 6 carbon atoms substituted by hydroxyl;

$R_3$ is aryl, unsubstituted or substituted by 1 to 3 members selected from the group consisting of 1 to 3 nitro moieties, 1 or 2 cyano moieties, 1 to 3 halogen atoms, 1 or 2 hydroxyl moieties, 1 or 2 acyloxy moieties of 1 or 2 carbon atoms in the acyl portion, 1 to 3 alkoxy moieties of 1 to 4 carbon atoms, a dioxymethylene moiety of the formula:

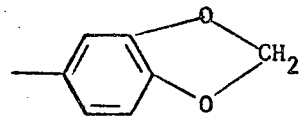

an alkylmercapto moiety of 1 to 4 carbon atoms in the alkyl portion, trifluoromethyl, carboxyl, carbalkoxy of 1 to 4 carbon atoms in the alkoxy portion and an alkyl-sulphonyl moiety of 1 to 4 carbon atoms in the alkyl portion; benzyl; styryl; pyridyl; pyrimidyl; furyl; thienyl; pyrrolyl; pyridyl, pyrrolyl, thienyl or furyl substituted by alkyl of 1 to 2 carbon atoms; or pyrimidyl substituted by at least one member selected from the group consisting of alkyl of 1 or 2 carbon atoms, 1 or 2 methoxy moieties and 1 or 2 ethoxy moieties; and $R_4$ is straight or branched chain alkyl of 1 to 4 carbon atoms, are useful for their coronary dilating effect, their nitrite-like effect on the heart, their anti-fibrillation effect, their vascular-spasmolytic effect and muscular-spasmolytic effect, and as anti-hypertensives.

41 Claims, No Drawings

SPASMOLYTIC, VASO-DILATING AND ANTI-HYPERTENSIVE COMPOSITIONS AND METHODS

This is a division of application Ser. No. 344,277 filed Mar. 23, 1973, now abandoned, which is a division of application Ser. No. 107,849, filed Jan. 19, 1971, which issued as U.S. Pat. No. 3,775,422 on Nov. 27, 1973.

The present invention is concerned with 1,4-dihydropyridines, processes for their production, pharmaceutical compositions embodying said 1,4-dihydropyridines as the active ingredient and methods of administration which utilize the administration of said 1,4-dihydropyridines orally or parenterally.

More particularly, the present invention relates to 1,4-dihydropyridines of the formula:

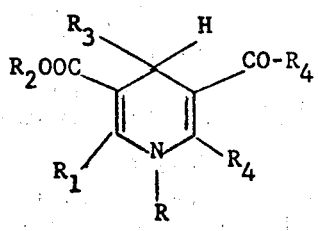

(1)

wherein
R is hydrogen, straight, branched or cyclic lower alkyl, lower alkenyl, or lower alkinyl, unsubstituted or substituted by hydroxyl or alkoxy of 1 to 3 carbon atoms; or benzyl, or phenethyl, unsubstituted or substituted in the aryl portion by 1 to 7 members selected from the group consisting of 1 to 3 alkoxy moieties of 1 to 3 carbon atoms, 1 or 2 alkyl moieties of 1 to 3 carbon atoms, and 1 or 2 halogen atoms;

$R_1$ is straight or branched chain alkyl of 1 to 4 carbon atoms;

$R_2$ is straight or branched chain alkyl of 1 to 6 carbon atoms, straight or branched chain dialkyl of 1 to 6 carbon atoms, straight or branched chain alkenyl of 2 to 6 carbon atoms, straight or branched chain alkinyl of 2 to 6 carbon atoms, cyclic alkyl of 3 to 6 carbon atoms, cyclic alkenyl of 3 to 6 carbon atoms, straight or branched chain alkyl or alkenyl of 2 to 6 carbon atoms interrupted by 1 or 2 oxygen atoms, straight or branched chain alkyl of 1 to 6 carbon atoms substituted by hydroxyl, or straight or branched chain alkenyl of 2 to 6 carbon atoms substituted by hydroxyl;

$R_3$ is aryl, unsubstituted or substituted by 1 to 3 members selected from the group consisting of 1 to 3 nitro moieties, 1 or 2 cyano moieties, 1 to 3 halogen atoms, 1 or 2 hydroxyl moieties, 1 or 2 acyloxy moieties of 1 or 2 carbon atoms in the acyl portion, 1 to 3 alkoxy moieties of 1 to 4 carbon atoms, a dioxymethylene moiety of the formula:

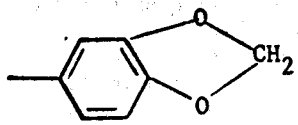

an alkylmercapto moiety of 1 to 4 carbon atoms in the alkyl portion, trifluoromethyl, carboxyl, carbalkoxy of 1 to 4 carbon atoms in the alkoxy portion and an alkyl-sulphonyl moiety of 1 to 4 carbon atoms in the alkyl portion; benzyl, styryl; pyridyl; pyrimidyl; furyl; thienyl; pyrrolyl; pyridyl, pyrrolyl, thienyl or furyl substituted by alkyl of 1 or 2 carbon atoms; or pyrimidyl substituted by at least one member selected from the group consisting of alkyl of 1 or 2 carbon atoms, 1 or 2 methoxy moieties and 1 or 2 ethoxy moieties; and $R_4$ is straight or branched chain alkyl of 1 to 4 carbon atoms.

These compounds are useful as coronary dilators, for their nitrite-like effect on the heart, as anti-fibrillation agents, for their vascular-spasmolytic and muscular-spasmolytic effect, and as anti-hypertensives.

The compounds of the present invention may be produced by reacting a xylidene derivative of the formula:

(2)

wherein $R_3$ and $R_4$ are as above defined, either (a) with a β-keto compound of the formula:

(3)

wherein $R_1$ and $R_2$ are as above defined, with ammonia or an amine of the formula:

(4)

wherein R is as above defined, or a salt thereof, or (b) with an enamine of the formula:

(5)

wherein R, $R_1$ and $R_2$ are as above defined, at an elevated temperature preferably from about 70°C. to about 120°C. in the presence of at least one organic solvent, such as an alcohol, glacial acetic acid, pyridine, dioxane, dimethylformamide, dimethylsulphoxide or a halogenated hydrocarbon. When an organic solvent is used, it is preferred to carry out the reaction at approximately the boiling point of the solvent or of the solvent mixture.

The xylidene derivatives of the formula (2) above are produced by condensing an aldehyde with an α,β-diketone.

The compounds of the present invention may also be produced by reacting a xylidene derivative of the formula:

(6)

wherein $R_1$, $R_2$ and $R_3$ are as above defined, either (a) with a β-keto compound of the formula:

(7)

an ammonia or an amine of the formula:

 (4)

wherein R is as above defined, or a salt thereof; or (b) with an enamine of the formula:

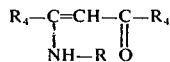 (8)

wherein R and $R_4$ are as above defined under the reaction conditions above set forth.

These xylidene derivatives of the formula (6) above can be produced by condensing an aldehyde with an acyl-fatty acid ester.

When R in formula (1) above is other than hydrogen, the compounds of the present invention may be produced according to a process carried out in the presence of pyridine, which process is set forth in co-pending application U.S. Ser. No. 35,574, filed May 7, 1970.

An alternate procedure for producing compounds of the present invention is described in Helv. chim. Acta 41 (1958) 2066 wherein when the compounds of formula (1) have R as hydrogen, 1,4-dihydropyridines are oxidized with suitable oxidizing agents, the resulting pyridine derivatives are quaternized with alkyl esters, and these esters are reduced to the corresponding 1,4-dihydropyridines with suitable reducing agents.

Suitable reactants for use in the processes of the present invention and for the production of the compounds of the present invention include as illustrative examples the following:

Aldehydes

Benzaldehyde, 2-, 3- or 4-hydroxybenzaldehyde, 2,4- or 2,6-dihydroxybenzaldehyde, 2-, 3- or 4-methoxybenzaldehyde, 2-isopropoxybenzaldehyde, 3-butoxybenzaldehyde, 3,4,5-trimethoxybenzaldehyde, 2-, 3- or 4-chloro or bromo or fluorobenzaldehyde, 2,4- or 2,6-dichlorobenzaldehyde, 2-methylbenzaldehyde, 2,4-dimethylbenzaldehyde, 3,5-diisopropyl-4-hydroxybenzaldehyde, 2-, 3- or 4-nitrobenzaldehyde, 2,4- or 2,6-dinitrobenzaldehyde, 2-nitro-6-bromobenzaldehyde, 2-nitro-3-methoxy-6-chlorobenzaldehyde, 2-nitro-3-hydroxy-4-chlorobenzaldehyde, 3-nitro-4-hydroxybenzaldehyde, 2-nitro-5-hydroxybenzaldehyde, 2-nitro-4-chlorobenzaldehyde, 2-nitro-4-methoxybenzaldehyde, 2-nitro-5-methoxybenzaldehyde, 2-, 3- or 4-trifluoromethylbenzaldehyde, 2-, 3- or 4-cyanobenzaldehyde, 2-nitro-4-cyanobenzaldehyde, 3-chloro-4-cyanobenzaldehyde, benzaldehyde-2-(3- or 4-)-sulphonic acid, 5-nitrobenzaldehyde-2-sulphonic acid, benzaldehyde-2-(3- or 4-) carboxylic acid, benzaldehyde-2-carboxylic acid ethyl ester, benzaldehyde-3-carboxylic acid isopropyl ester, benzaldehyde-4-carboxylic acid butyl ester, 2-nitrobenzaldehyde-4-carboxylic acid, 3-nitrobenzaldehyde-4-carboxylic acid ethyl ester, cinnamaldehyde, hydrocinnamaldehyde, 2-, 3- or 4-methylmercaptobenzaldehyde, 2-methylmercapto-5-nitrobenzaldehyde, 2-butylmercaptobenzaldehyde, 2-, 3- or 4-methylsulphinylbenzaldehyde, 2-, 3- or 4-methylsulphonylbenzaldehyde, cinnamaldehyde, dihydrocinnamaldehyde, formylcyclohexane, 1-formyl-cyclohexene-3, 1-formyl-cyclohexine-1,3, 1-formylcyclopentene-3, $\alpha,\beta$- or $\gamma$-pyridinaldehyde, 6-methylpyridine-2-aldehyde, pyrimidine-5-aldehyde, 4,6-dimethoxy-pyrimidine-5-aldehyde, furan-2-aldehyde, thiophen-2-aldehyde and pyrrol-2-aldehyde.

Acyl-Fatty Acid Esters

Formylacetic acid ethyl ester, formylacetic acid butyl ester, acetoacetic acid methyl ester, acetoacetic acid ethyl ester, acetoacetic acid propyl ester, acetoacetic acid isopropyl ester, acetoacetic acid-($\alpha$- or $\beta$=) hydroxyethyl ester, acetoacetic acid ($\alpha$- or $\beta$-) methoxyethyl ester, acetoacetic acid ($\alpha$- or $\beta$)-ethoxyethyl ester, acetoacetic acid($\alpha$- or $\beta$-) propoxyethyl ester, acetoacetic acid furfuryl ester, acetoacetic acid tetrahydrofurfuryl ester, acetoacetic acid allyl ester, acetoacetic acid propargyl ester, acetoacetic acid cyclohexyl ester, propionylacetic acid ethyl ester, butyrylacetic acid ethyl ester and isobutyrylacetic acid ethyl ester.

Diones

Pentanedione-(2,4), heptanedione-(3,5), nonanedione-(4,6) and 2,6-dimethyl-heptanedione-(3,5).

Amines

Methylamine, ethylamine, propylamine, isopropylamine, butylamine, allylamine, propargylamine, 1-hydroxyethylamine-2, 1,3-dihydroxyisopropylamine, cyclohexylamine, benzylamine, 4-chlorobenzylamine, 3,4-dimethoxybenzylamine and phenethylamine.

According to a preferred embodiment of the present invention R is hydrogen, alkyl of 1 to 6 carbon atoms, benzyl or phenethyl, $R_1$ is straight or branched chain alkyl of 1 to 4 carbon atoms, $R_2$ is mono- or dialkyl of 1 to 6 carbon atoms, alkinyl of 2 to 6 carbon atoms, cyclic alkyl of 3 to 6 carbon atoms, alkyl of 2 to 6 carbon atoms interrupted by oxygen, or cyclic alkyl of 3 to 6 carbon atoms wherein the ring contains oxygen as a heteroatom, $R_3$ is benzyl; phenyl unsubstituted or substituted by 1 or 2 nitro moieties, cyano moieties, halogen atoms especially fluorine, chlorine or bromine, alkoxy moieties of 1 to 3 carbon atoms or trifluoromethyl; pyridyl, pyrrolyl, furyl or thienyl unsubstituted or substituted by alkyl of 1 or 2 carbon atoms; or pyrimidyl unsubstituted or substituted by alkyl of 1 or 2 carbon atoms, 1 or 2 methoxy moieties, or 1 or 2 ethoxy moieties; and $R_4$ is alkyl of 1 to 4 carbon atoms.

The 1,4-dihydropyridines of the present invention have a broad range of utility as indicated above and the following effects have been exhibited in animal experiments:

1. The compounds produce a distinct and long-lasting dilation of the coronary vessels on parenteral, oral and perlingual administration. This action on the coronary vessels is intensified by a simultaneous, nitrite-like, effect of reducing the load on the heart.

They influence or modify the heart metabolism in the sense of a saving of energy.

2. The excitability of the stimulus-forming and stimulus-conducting system within the heart is lowered, so that an anti-fibrillation action, demonstrable in therapeutic doses, results.

3. The tonus of the smooth muscles of the vessels is greatly reduced under the action of the compounds. This vascular-spasmolytic action can occur in the total vascular system or can manifest itself to a more or less isolated extent in circumscribed vascular regions (such as for example the central-nervous system).

4. The compounds reduce the blood pressure of normal tonic and hypertonic animals and can thus be used as anti-hypertensive agents.

5. The compounds have strong muscular-spasmolytic actions, which manifest themselves on the smooth muscle of the gastro-intestinal tract, the urogenital tract, and the respiratory system.

According to the present invention, pharmaceutical compositions are produced which comprise a compound of the present invention or more than one compound of the present invention in combination with a pharmaceutically acceptable non-toxic inert diluent or carrier. The present invention further includes a medicament in unit dosage form which comprises a compound of the present invention or more than one compound of the present invention per se or in combination with a pharmaceutically acceptable non-toxic inert diluent or carrier. The medicament may include a protective envelope containing the active compound or compounds, and if present, the pharmaceutically acceptable non-toxic inert diluent or carrier.

The term "medicament in unit dosage form" as used above means a medicament as defined above in the form of discrete portions each containing a unit dosage, or a multiple or sub-multiple of a unit dose of the active compound or compounds, for example two, three or four unit doses or a half, a third or a fourth of a unit dose. Such portions may, for example, be in monolithic coherent form, such as tablets, suppositories, pills or dragees; in wrapped or concealed form, such as wrapped powders, cachets, sachets or capsules; in ampoules, either free or as a sterile solution suitable for parenteral injection; or in any other form known to the art.

The 1,4-dihydropyridines of the formula (1) can be administered orally or parenterally.

In general, it has proved advantageous to administer amount of about 0.01 mg to about 100 mg, preferably about 0.1 to 50 mg per kg body weight and per day, in order to achieve satisfactory results. Nevertheless, it may sometimes be necessary to deviate from the above ranges, depending on the body weight of the treated person or the method of application. In some cases it may be sufficient to use less than the minimum amount stated above, whereas in other cases the aforesaid upper limit will have to be exceeded. If larger amounts are applied, it may be advisable to distribute these in several individual doses over the day.

The compounds of formula (1) can be administered as such or as pharmaceutical compositions as described above. Suitable forms of application in combination with various inert carriers are: tablets, capsules, dragees, ampoules, powders, sprays, aqueous suspensions, injectable solutions, elixirs, syrups and the like. Such carriers comprise solid diluents or fillers, a sterile aqueous medium as well as various non-toxic organic solvents and the like. Tablets and the like intended or oral application may, of course, be provided with sweetening additives and similar substances. In the aforesaid case the therapeutically active compound should be present at a concentration of about 0.5 to 90 per cent by weight of the total mixture, in quantities which are sufficient to achieve the range of dosage, mentioned above.

In the case of oral administration, the tablets or capsules may also contain additives, such as sodium citrate, calcium carbonate and dicalcium phosphate together with various other additives, such as starch, preferably potato starch, and the like, and binding agents, such as polyvinyl-pyrrolidone, gelatin and the like. Lubricants, such as magnesium stearate, sodium lauryl sulphate and talc may also be added for the production of tablets. In the case of aqueous suspensions and/or elixirs which are intended for oral application, the active substance may be used with various flavouring agents, coloring substances, emulsifiers and/or together with diluents, such as water, ethanol, propylene glycol, glycerol and similar compounds or combinations of this type.

In the case of parenteral administration, solutions of the active substances in sesame or peanut oil or in aqueous propylene glycol or N,N-dimethyl formamide can be used, as can sterile aqueous solutions in the case of the water-soluble compounds. Aqueous solutions of this type should be buffered in the usual way, when required, and the liquid diluent should previously be rendered isotonic by the addition of the necessary amount of salt or glucose. These aqueous solutions are particularly suitable for intravenous and intraperieoneal injections. Sterile aqueous media of this type may be prepared in a manner per se known.

The 1,4-dihydropyridines of the present invention are particularly useful because they are suitable for oral administration. Therefore, pharmaceutical compositions in orally administrable form are the preferred embodiment of the pharmaceutical compositions. The following table sets forth a range of viable dosages for compounds representative of those of the present invention:

LIST OF DOSAGE RATES

| Compound | Dosage rate in mg/kg i.v. application |
| --- | --- |
| Example 1 | 0.3 – 0.5 |
| Compound a) | 0.5 – 2.0 |
| Compound b) | 0.1 – 0.5 |
| Compound c) | 0.03 – 0.1 |
| Example 5 | 0.5 – 1.0 |
| Compound a) | 3.0 – 5.0 |
| Example 6 | 1.0 – 3.0 |

The compound of Example 1 has exhibited good activity when administered orally at a dosage range of from 1 to about 50 mg/kg.

The following non-limitative examples more particularly illustrate the present invention.

EXAMPLE 1

4-(2'-Pyridyl)-2,6-dimethyl-3-aceto-1,4-dihydropyridine-5-carboxylic acid ethyl ester After stirring a solution of 21.4 g of pyridin-2-aldehyde and 20 g of acetylacetone in 250 ccs. of benzene, with the addition of 2 ccs. of piperidine for approx. 12 hours at room temperature, the water is separated off, the solution is dried and the solvent is distilled off in vacuo.

The residue, pyrid-(2)-al acetylacetone, is heated for 5 hours on a waterbath with 26 g of β-aminocrotonic acid ethyl ester, and the reaction product (named above) is treated with ether, cooled, filtered off and re-crystallized from 250 ccs of alcohol.

20 g of yellow crystals of melting point 175°C.

The following compounds were prepared in an analogous manner from the reactants specified:

a. 4-(3'-pyridyl)-2,6-dimethyl-3-aceto-1,4-dihydropyridine-5-carboxylic acid ethyl ester of melting point 188°C from pyridal-(3)-acetylacetone and β-aminocrotonic acid ethylester.

4-phenyl-2,6-dimethyl-3-aceto-1,4-dihydropyridine-5-carboxylic acid diethyl ester, melting point 167°C, from benzalacetylacetone and β-aminocrotonic acid ethylester.

c. 4-(2'-nitrophenyl)-2,6-dimethyl-3-aceto-1,4-dihydropyridine-5-carboxylic acid ethyl ester of melting point 174° – 176°C, from 2-nitrobenzal-acetylacetone and β-aminocrotonic acid ethylester.

Example 2

The following compounds were produced by a procedure analogous to that described in Example 1 from the reactants specified:

a. 4-(2'-cyanophenyl)-2,6-dimethyl-3-aceto-1,4-dihydropyridine-5-carboxylic acid ethyl ester, melting point 184°C, from 2-cyanobenzal-acetylacetone and β-aminocrotonic and ethylester.

b. 4-(3'-nitrophenyl)-2,6-dimethyl-3-aceto-1,4-dihydropyridine-5-carboxylic acid methyl ester, melting point 200°C, from 3-nitrobenzal-acetylacetone and β-aminocrotonic and methylester.

c. 4-(2'-fluorophenyl)-2,6-dimethyl-3-aceto-1,4-dihydropyridine-5-carboxylic acid methyl ester, melting point 177°C, from 2-fluorbenzal acetylacetone and β-aminocrotonic acid methylester.

d. 4-(2'-trifluoromethylphenyl)-2,6-dimethyl-3-aceto-1,4-dihydropyridine-5-carboxylic acid ethyl ester, melting point 141° to 143°C, from 2-trifluoromethyl-benzal-acetylacetone and B-aminocrotonic acid ethylester.

e. 4-(3'-trifluoromethylphenyl)-2,6-dimethyl-3-aceto-1,4-dihydropyridine-5-carboxylic acid methyl ester, melting point 170°C, from 3-Trifluormethylbenzal-acetylacetone and β-aminocrotonic acid methylester.

f. 4-(3'-nitro-4'-chlorophenyl)-2,6-dimethyl-3-aceto-1,4-dihydropyridine-5-carboxylic acid methyl ester, melting point 177°C, from 3-nitro-4-chlorbenzal-acetylacetone and β-aminocrotonic acid methyl ester.

g. 4-phenyl-2,6-dimethyl-3-aceto-1,4-dihydropyridine-5-carboxylic acid β-methoxyethyl ester (oil) from benzal-acetylacetone, acetoacetic acid β-methoxyethyl ester and ammonia.

h. 4-phenyl-2,6-dimethyl-3-aceto-1,4-dihydropyridine-5-carboxylic acid furfuryl ester (oil) from benzal-acetylacetone, acetoacetic acid furfuryl ester ammonia.

i. 4-phenyl-2,6-dimethyl-3-aceto-1,4-dihydropyridine-5-carboxylic acid propargyl ester, melting point 199°C, from benzal-acetylacetone, acetoacetic acid propargyl ester ammonia.

EXAMPLE 3

4-Phenyl-2,6-dimethyl-3-aceto-1,4-dihydropyridine-5-carboxylic acid ethyl ester (identical to Example 1 b)

0.1 mol of benzalacetic acid ethyl ester (obtained from 10.6 g of benzaldehyde and 13 g of acetoacetic acid ethyl ester in benzene with the addition of piperidine) is heated for 3 – 4 hours with 10 g of 2-aminopenten-(2)-one-(4) to 90° – 100°, after cooling the solid reaction product is taken up in a little ether, and after filtering off and recrystallizing, yellow crystals of melting point 167°C (alcohol) are obtained.

EXAMPLE 4

4-(2'-methylphenyl)-2,6-dimethyl-3-aceto-1,4-dihydropyridine-5-carboxylic acid ethyl ester (melting point 155°C) was prepared by a method analogous to that described in Example 3 from 2-methylbenzal-acetylacetone and β-Aminocrotonic acid ethyl ester.

EXAMPLE 5

4-(4'-Pyrimidyl)-2,6-dimethyl-3-aceto-1,4-dihydropyridine-5-carboxylic acid ethyl ester 1 cc. of piperidine is added to a solution of 10 g of pyrimidine-4-aldehyde and 10 g of acetylacetone in 150 ccs. of benzene, the mixture is stirred for 48 hours at room temperature, the water is then separated off, the solution is dried and evaporated, and the residue (pyrimid-4-al-acetylacetone) is heated with 13 g of β-aminocrotonic acid ethyl ester for 5 hours on a water-bath.

After addition of some ether, 13 g of yellow crystals of melting point 183° – 185°C (alcohol) are obtained.

The 4-(4',6'-dimethoxy-5'-pyrimidyl)-2,6-dimethyl-3-aceto-1,4-dihydropyridine-5-carboxylic acid ethyl ester, melting point 236° – 239°C, is obtained in the same manner, from 4,6-dimethoxypyrimid-5-al-acetylacetone and β-Aminocrotonic-acid ethylester.

EXAMPLE 6

N-methyl-4-phenyl-2,6-dimethyl-3-aceto-1,4-dihydropyridine-5-carboxylic acid methyl ester 0.1 mol of benzalacetylacetone (prepared analogously to pyrid-(2)-al acetylacetone in Example 1) is heated with 12 ccs. of acetoacetic acid methyl ester and 8 g of methylamine hydrochloride in 25 ccs. of pyridine to 90° – 100° for 1 hour, the mixture is poured into ice water, and after filtering off and recrystallizing from 500 ccs. of methanol, yellow crystals of melting point 187°C are obtained.

EXAMPLE 7

The following compounds were produced by a procedure analogous to that described in Example 6 from the reactants specified:

a. N-methyl-4-(3'-nitro-4'-chlorophenyl)-2,6-dimethyl-3-aceto-1,4-dihydropyridine-5-carboxylic acid methyl ester, melting point 118°C, from 3-nitro-4-chlorbenzal acetylacetone, acetoacetic acid methyl ester and methylaminhydrochloride.

b. N-methyl-(3'-nitro-4'-chlorophenyl)-2,6-dimethyl-3-aceto-1,4-dihydropyridine-5-carboxylic acid propargyl ester, melting point 140°C, from 3-nitro-4-chlorbenzal-acetylacetone, acetoacetic acid propargyl ester and methylamino-hydrochloride.

c. N-methyl-4-(3'-nitrophenyl)-2,6-dimethyl-3-aceto-1,4-dihydropyridine-5-carboxylic acid methyl ester, melting point 147°C, from 3-nitrobenzal-acetylacetone, acetoacetic acid methyl ester and methylamino-hydrochloride.

What is claimed is:

1. A pharmaceutical composition capable of producing spasmolytic, vascular dilating, and antihypertensive effects upon administration to a human or other animal which comprises an effective amount of a 1,4-dihydropyridine of the formula:

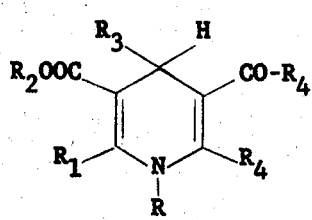

wherein
- R is hydrogen or straight chain lower alkyl;
- $R_1$ is straight or branched chain alkyl of 1 to 4 carbon atoms;
- $R_2$ is straight or branched chain alkyl of 1 to 6 carbon atoms, straight or branched chain alkyl of 2 to 6 carbon atoms interrupted by 1 oxygen atom, furfuryl or propargyl;
- $R_3$ is phenyl, benzyl or phenyl substituted by a member selected from the group consisting of nitro, cyano, halogen, trifluoromethyl, nitro and chloro, 1 or 2 alkoxy moieties of 1 to 2 carbon atoms, and a dioxymethylene moiety of the formula:

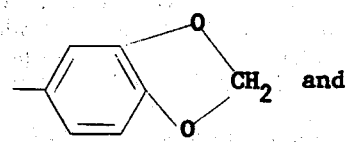 and

- $R_4$ is straight chain alkyl of 1 to 4 carbon atoms.

2. A pharmaceutical composition according to claim 1 wherein
- R is hydrogen or methyl;
- $R_1$ is methyl;
- $R_2$ is methyl, ethyl, diethyl, β-methoxyethyl, propargyl or furfuryl;
- $R_3$ is phenyl, nitrophenyl, cyanophenyl, fluorophenyl, trifluoromethylphenyl, benzyl, or nitrochlorophenyl; and
- $R_4$ is methyl.

3. A pharmaceutical composition according to claim 1 in oral dosage unit form.

4. A composition according to claim 1 wherein the 1,4-dihydropyridine is 4-phenyl-2,6-dimethyl-3-aceto-1,4-dihydropyridine-5-carboxylic acid diethyl ester.

5. A composition according to claim 1 wherein the 1,4-dihydropyridine is 4-(2'-nitrophenyl)-2,6-dimethyl-3-aceto-1,4-dihydropyridine-5-carboxylic acid ethyl ester.

6. A composition according to claim 1 wherein the 1,4-dihydropyridine is 4-(2'-cyanophenyl)-2,6-dimethyl-3-aceto-1,4-dihydropyridine-5-carboxylic acid ethyl ester.

7. A composition according to claim 1 wherein the 1,4-dihydropyridine is 4-(3'-nitrophenyl)-2,6-dimethyl-3-aceto-1,4-dihydropyridine-5-carboxylic acid methyl ester.

8. A composition according to claim 1 wherein the 1,4-dihydropyridine is 4-(2'-fluorophenyl)-2,6-dimethyl-3-aceto-1,4-dihydropyridine-5-carboxylic acid methyl ester.

9. A composition according to claim 1 wherein the 1,4-dihydropyridine is 4-(2'-trifluoromethylphenyl)-2,6-dimethyl-3-aceto-1,4-dihydropyridine-5-carboxylic acid ethyl ester.

10. A composition according to claim 1 wherein the 1,4-dihydropyridine is 4-(3'-trifluoromethylphenyl)-2,6-dimethyl-3-aceto-1,4-dihydropyridine-5-carboxylic acid methyl ester.

11. A composition according to claim 1 wherein the 1,4-dihydropyridine is 4-(3'-nitro-4'-chlorophenyl)-2,6-dimethyl-3-aceto-1,4-dihydropyridine-5-carboxylic acid methyl ester.

12. A composition according to claim 1 wherein the 1,4-dihydropyridine is 4-phenyl-2,6-dimethyl-3-aceto-1,4-dihydropyridine-5-carboxylic acid β-methoxyethyl ester.

13. A composition according to claim 1 wherein the 1,4-dihydropyridine is 4-phenyl-2,6-dimethyl-3-aceto-1,4-dihydropyridine-5-carboxylic acid furfuryl ester.

14. A composition according to claim 1 wherein the 1,4-dihydropyridine is 4-phenyl-2,6-dimethyl-3-aceto-1,4-dihydropyridine-5-carboxylic acid propargyl ester.

15. A composition according to claim 1 wherein the 1,4-dihydropyridine is 4-phenyl-2,6-dimethyl-3-aceto-1,4-dihydropyridine-5-carboxylic acid ethyl ester.

16. A composition according to claim 1 wherein the 1,4-dihydropyridine is 4-(2'-methylphenyl)-2,6-dimethyl-3-aceto-1,4-dihydropyridine-5-carboxylic acid ethyl ester.

17. A composition according to claim 1 wherein the 1,4-dihydropyridine is N-methyl-4-phenyl-2,6-dimethyl-3-aceto-1,4-dihydropyridine-5-carboxylic acid methyl ester.

18. A composition according to claim 1 wherein the 1,4-dihydropyridine is N-methyl-4-(3'-nitro-4'-chlorophenyl)-2,6-dimethyl-3-aceto-1,4-dihydropyridine-5-carboxylic acid methyl ester.

19. A composition according to claim 1 wherein the 1,4-dihydropyridine is N-methyl-(3'-nitro-4'-chlorophenyl)-2,6-dimethyl-3-aceto-1,4-dihydropyridine-5-carboxylic acid propargyl ester.

20. A composition according to claim 1 wherein the 1,4-dihydropyridine is N-methyl-4-(3'-nitrophenyl)-2,6-dimethyl-3-aceto-1,4-dihydropyridine-5-carboxylic acid methyl ester.

21. The method of producing spasmolytic, vascular dilating and antihypertensive effects in a human or other animal which comprises administering thereto a 1,4-dihydropyridine of the formula:

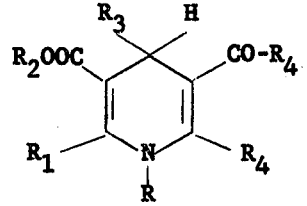

wherein
- R is hydrogen or straight chain lower alkyl;
- $R_1$ is straight or branched chain alkyl of 1 to 4 carbon atoms;
- $R_2$ is straight or branched chain alkyl of 1 to 6 carbon atoms, straight or branched chain alkyl of 2 to 6 carbon atoms interrupted by 1 oxygen atom, furfuryl or propargyl;
- $R_3$ is phenyl, benzyl or phenyl substituted by a member selected from the group consisting of nitro, cyano, halogen, trifluoromethyl, nitro and chloro, 1 or 2 alkoxy moieties of 1 or 2 carbon atoms, and a dioxymethylene moiety of the formula:

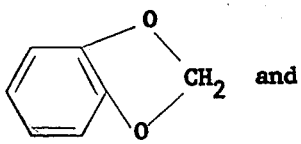

R₄ is straight chain alkyl of 1 to 4 carbon atoms.

22. The method according to claim 21 wherein
R is hydrogen or methyl;
R₁ is methyl;
R₂ is methyl, ethyl, diethyl, β-methoxyethyl, propargyl or furfuryl;
R₃ is phenyl, nitrophenyl, cyanophenyl, fluorophenyl, trifluoromethylphenyl, benzyl or nitrochlorophenyl; and
R₄ is methyl.

23. The method according to claim 21 wherein said 1,4-dihydropyridine is administered orally.

24. The method according to claim 21 wherein the daily dosage administered is from about 0.1 to about 50 mg/kg of body weight.

25. A method according to claim 21 wherein the 1,4-dihydropyridine is 4-phenyl-2,6-dimethyl-3-aceto-1,4-dihydropyridine-5-carboxylic acid diethyl ester.

26. A method according to claim 21 wherein the 1,4-dihydropyridine is 4-(2'-nitrophenyl)-2,6-dimethyl-3-aceto-1,4-dihydropyridine-5-carboxylic acid ethyl ester.

27. A method according to claim 21 wherein the 1,4-dihydropyridine is 4-(2'-cyanophenyl)-2,6-dimethyl-3-aceto-1,4-dihydropyridine-5-carboxylic acid ethyl ester.

28. A method according to claim 21 wherein the 1,4-dihydropyridine is 4-(3'-nitrophenyl)-2,6-dimethyl-3-aceto-1,4-dihydropyridine-5-carboxylic acid methyl ester.

29. A method according to claim 21 wherein the 1,4-dihydropyridine is 4-(2'-fluorophenyl)-2,6-dimethyl-3-aceto-1,4-dihydropyridine-5-carboxylic acid methyl ester.

30. A method according to claim 21 wherein the 1,4-dihydropyridine is 4-(2'-trifluoromethylphenyl)-2,6-dimethyl-3-aceto-1,4-dihydropyridine-5-carboxylic acid ethyl ester.

31. A method according to claim 21 wherein the 1,4-dihydropyridine is 4-(3'-trifluoromethylphenyl)-2,6-dimethyl-3-aceto-1,4-dihydropyridine-5-carboxylic acid methyl ester.

32. A method according to claim 21 wherein the 1,4-dihydropyridine is 4-(3'-nitro-4'-chlorophenyl)-2,6-dimethyl-3-aceto-1,4-dihydropyridine-5-carboxylic acid methyl ester.

33. A method according to claim 21 wherein the 1,4-dihydropyridine is 4-phenyl-2,6-dimethyl-3-aceto-1,4-dihydropyridine-5-carboxylic acid β-methoxyethyl ester.

34. A method according to claim 21 wherein the 1,4-dihydropyridine is 4-phenyl-2,6-dimethyl-3-aceto-1,4-dihydropyridine-5-carboxylic acid furfuryl ester.

35. A method according to claim 21 wherein the 1,4-dihydropyridine is 4-phenyl-2,6-dimethyl-3-aceto-1,4-dihydropyridine-5-carboxylic acid propargyl ester.

36. A method according to claim 21 wherein the 1,4-dihydropyridine is 4-phenyl-2,6-dimethyl-3-aceto-1,4-dihydropyridine-5-carboxylic acid ethyl ester.

37. A method according to claim 21 wherein the 1,4-dihydropyridine is 4-(2'-methylphenyl)-2,6-dimethyl-3-aceto-1,4-dihydropyridine-5-carboxylic acid ethyl ester.

38. A composition according to claim 21 wherein the 1,4-dihydropyridine is N-methyl-4-phenyl-2,6-dimethyl-3-aceto-1,4-dihydropyridine-5-carboxylic acid methyl ester.

39. A composition according to claim 21 wherein the 1,4-dihydropyridine is N-methyl-4-(3'-nitro-4'-chlorophenyl)-2,6-dimethyl-3-aceto-1,4-dihydropyridine-5-carboxylic acid methyl ester.

40. A composition according to claim 21 wherein the 1,4-dihydropyridine is N-methyl-(3'-nitro-4'-chlorophenyl)-2,6-dimethyl-3-aceto-1,4-dihydropyridine-5-carboxylic acid propargyl ester.

41. A composition according to claim 21 wherein the 1,4-dihydropyridine is N-methyl-4-(3'-nitrophenyl)-2,6-dimethyl-3-aceto-1,4-dihydropyridine-5-carboxylic acid methyl ester.

* * * * *